US006456734B1

(12) United States Patent
Youvan et al.

(10) Patent No.: US 6,456,734 B1
(45) Date of Patent: Sep. 24, 2002

(54) CALIBRATION OF FLUORESCENCE RESONANCE ENERGY TRANSFER IN MICROSCOPY

(75) Inventors: Douglas C. Youvan, San Jose; Christopher M. Silva, Sunnyvale; Edward J. Bylina, San Jose; William J. Coleman, Moutain View; Michael R. Dilworth, Santa Cruz; Mary M. Yang, San Jose, all of CA (US)

(73) Assignee: Kairos Scientific, Inc., San Diego, CA (US)

( * ) Notice: Subject to any disclaimer, the term of this patent is extended or adjusted under 35 U.S.C. 154(b) by 0 days.

(21) Appl. No.: 09/092,316

(22) Filed: Jun. 5, 1998

Related U.S. Application Data

(60) Provisional application No. 60/048,696, filed on Jun. 5, 1997, and provisional application No. 60/057,931, filed on Sep. 4, 1997.

(51) Int. Cl.$^7$ ................................................. G06K 9/00
(52) U.S. Cl. ........................ 382/128; 382/100; 382/132; 382/133
(58) Field of Search ........................... 356/346; 435/18, 435/325, 29, 366, 6; 382/128, 100, 133, 132; 424/450; 514/2; 365/151

(56) References Cited

U.S. PATENT DOCUMENTS

| | | | | |
|---|---|---|---|---|
| 4,648,051 A | * | 3/1987 | Wandell et al. | ............. 364/526 |
| 5,121,436 A | | 6/1992 | Kasdan et al. | ............. 382/128 |
| 5,162,990 A | | 11/1992 | Odeyale et al. | ............. 382/128 |
| 5,331,551 A | * | 7/1994 | Tsuruoka et al. | ...... 364/413.13 |
| 5,556,959 A | * | 9/1996 | Brush et al. | ............. 536/25.32 |
| 5,732,150 A | | 3/1998 | Zhou et al. | ................. 382/133 |
| 5,784,162 A | * | 6/1998 | Cabib et al. | ................ 356/346 |
| 5,998,204 A | * | 12/1999 | Tsien et al. | ................ 435/325 |

OTHER PUBLICATIONS

Fundamentals of Electronic Image Processing, 1996.*

* cited by examiner

Primary Examiner—Leo Boudreau
Assistant Examiner—M. B Choobin
(74) Attorney, Agent, or Firm—McCutchen, Doyle, Brown & Enersen, LLP

(57) ABSTRACT

Imaging hardware, software, calibrants, and methods are provided to visualize and quantitate the amount of Fluorescence Resonance Energy Transfer (FRET) occurring between donor and acceptor molecules in epifluorescence microscopy. The MicroFRET system compensates for overlap among donor, acceptor, and FRET spectra using well characterized fluorescent beads as standards in conjunction with radiometrically calibrated image processing techniques. The MicroFRET system also provides precisely machined epifluorescence cubes to maintain proper image registration as the sample is illuminated at the donor and acceptor excitation wavelengths. Algorithms are described that pseudocolor the image to display pixels exhibiting radiometrically-corrected fluorescence emission from the donor (blue), the acceptor (green) and FRET (red). The method is demonstrated on samples exhibiting FRET between genetically engineered derivatives of the Green Fluorescent Protein (GFP) bound to the surface of Ni chelating beads by histidine-tags.

12 Claims, 9 Drawing Sheets

(5 of 9 Drawing Sheet(s) Filed in Color)

CALIBRATION OF FLUORESCENCE RESONANCE ENERGY TRANSFER IN MICROSCOPY

CLAIM OF PRIORITY

This application claims priority under 35 USC §119(e) to U.S. patent application Ser. No. 60/048,696, filed Jun. 5, 1997, and to U.S. patent application Ser. No. 60/057,931, filed Sep. 4, 1997.

STATEMENT AS TO FEDERALLY SPONSORED RESEARCH

This invention was made at least in part with funds from the Federal Government, Department of Energy. The Government may have certain rights in the invention.

TECHNICAL FIELD

This invention relates generally to fluorescence resonance energy transfer (FRET), and more particularly to calibration standards for FRET.

BACKGROUND

Fluorescence resonance energy transfer (FRET) is a non-radiative process whereby energy from a fluorescent donor molecule is transferred to an acceptor molecule without the involvement of a photon. Excitation of the donor molecule enhances the fluorescence emission of the longer-wavelength acceptor molecule (i.e., sensitized acceptor emission). The quantum yield of the donor fluorescence emission is concomitantly diminished. FRET has become a valuable tool for microscopy, because the efficiency of energy transfer has a strong inverse dependence on the distance between the donor and acceptor molecules. Thus, the appearance of FRET is a highly specific indicator of the proximity of the two molecules. This has led to the use of FRET efficiency as a "spectroscopic ruler" to measure molecular distances.

A typical FRET experiment for observing cells involves specifically labeling particular molecules with fluorescent dyes and detecting these dyes over selected excitation and emission wavelength ranges. These wavelength ranges are commonly referred to as "channels" for a particular fluorophore. Fluorescent labeling is easier to accomplish for extracellular molecules than for intracellular ones. For intracellular molecules, the dye conjugated molecules must be either injected into the cell for observation or the labeled molecules may be overlaid onto a thin section of fixed, permeabilized tissue. Recently, however, the availability of green fluorescent protein (GFP) mutants with shifted excitation and emission spectra has made it feasible to measure protein-protein interactions by using GFP tags as intracellular markers. GFP-tagged protein chimeras are expressed intracellularly and do not require any chemical treatment to become fluorescent. FRET can also occur between fusions of blue-emitting and green-emitting GFP variants.

Although FRET microscopy has the potential to become a widely used analytical tool in these systems, accurate steady-state measurement of FRET by standard epifluorescence microscopy has been hindered by several limitations, including:

(1) Bleed-through or spillover of donor (and isolated acceptor) fluorescence emission into the FRET channel due to spectral overlap. Compensation for spectral overlap requires the use of accurate calibration standards to determine the correction factors.

(2) Image registration. Correcting each pixel in an image for spectral overlap requires taking three separate images with each of the three epifluorescence cubes (i.e., donor emission, acceptor emission, and sensitized acceptor emission). If the surfaces of all three epifluorescence cubes are not exactly parallel, image registration is lost and the resultant geometric distortion will also have to be corrected. Loss of image registration greatly complicates the correction procedure and reduces the overall accuracy of the corrected data.

(3) Calculation of FRET by sensitized emission has a large uncertainty when the FRET efficiency is low.

(4) Photobleaching of the donor during the measurement results in anomalously low estimates of FRET in the sample.

These limitations apply to GFP as well as to other fluorescent FRET pairs.

Because of recent advances in "chromosome painting," cell biologists are becoming familiar with epifluorescence microscopes that utilize multi-bandpass filters to obtain information on several dyes simultaneously. Some of these instruments employ interferometry, while others use filter wheels in the excitation path to select specific excitation bands. In both cases, an assumption is made that excitation at a given wavelength results in emission from the next reddest transmission band. While multiband cubes help to solve the image registration problem for separable dyes, fluorescence phenomena which involve large or variable Stokes shifts cannot be addressed. Multiband systems cannot be used to detect FRET because the FRET emission channel is not the next (redder) emission band and is therefore indistinguishable from the donor's emission.

Accordingly, the inventors have determined that a need exists for an improved FRET system which provides for close image registration, and minimizes or corrects for low FRET efficiency, photobleaching, and spectral overlap. The present invention provides for such a system.

SUMMARY

The invention provides a method for transforming an initial image of biological material to a processed image, the initial image being represented by a set of pixels each having three color space coordinates. The method includes the steps of (a) selecting at least two image regions in the initial image, each image region including at least one pixel, wherein the image regions define at least two distinguishable spectral categories; (b) performing a color space transformation on the initial image, based on the color space coordinates of the pixels in each of the selected image regions, to generate a processed image; and (c) evaluating the processed image for a visible indication of an improved spatial distribution of color.

The invention further provides a quantitative method for color space transforming an initial FRET image of biological material to a corrected FRET image, and includes applying other image corrections.

The invention also provides a set of calibration targets for FRET. The set of calibration targets includes: (a) a pure donor target for binding only to donor molecules; (b) a pure acceptor target for binding only to acceptor molecules; and (c) a donor and acceptor target for binding to a mixture of donor and acceptor molecules which exhibit FRET. In a specific embodiment, the set of calibration targets are genetically engineered derivatives of the Green Fluorescent Protein (GFP) bound to the surface of Ni chelating beads by histidine-tags (His-tags).

The details of one or more embodiments of the invention are set forth in the accompanying drawings and the descrip-

3 tion below. Other features, objects, and advantages of the invention will be apparent from the description and drawings, and from the claims.

DESCRIPTION OF DRAWINGS

The file of this patent contains at least one drawing executed in color. Copies of this patent with color drawings will be provided by the Patent and Trademark Office upon request and payment of the necessary fee.

DETAILED DESCRIPTION

Overview

Figures 1A, 1B:
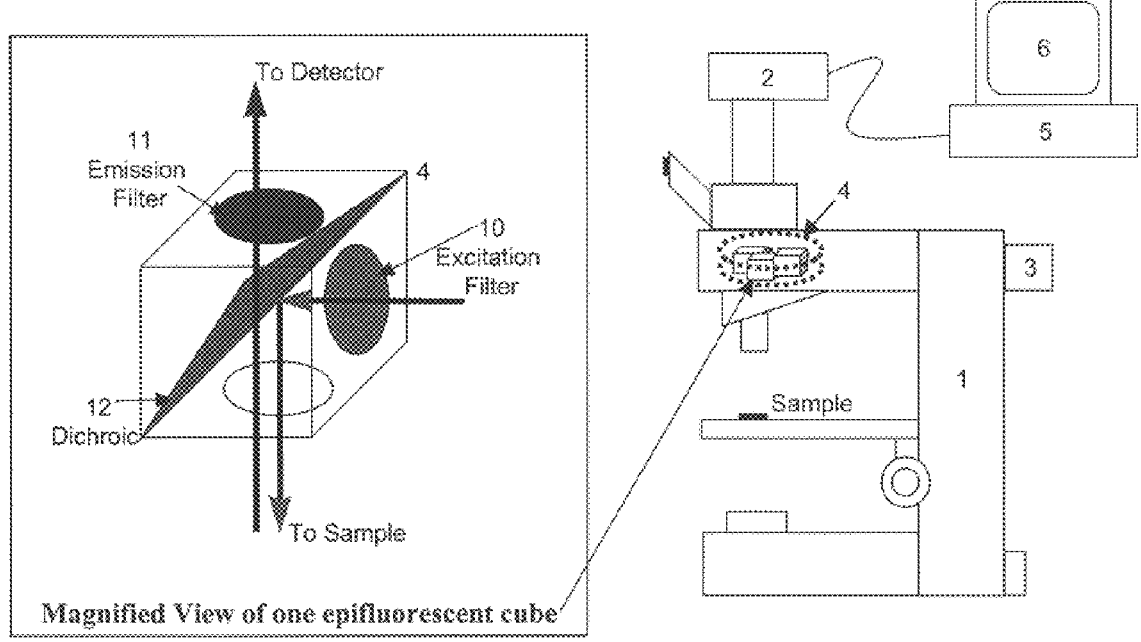
FIG. 1a is a block diagram showing one embodiment of a FRET imaging microscope for acquiring spatially co-registered electronic images suitable for use with the present invention.
FIG. 1b is a diagram of an epifluorescence filter cube.

The invention provides a new system for FRET imaging microscopy, based on epifluorescence microscopy. In a preferred embodiment known as the MicroFRET system, precisely machined epifluorescence cubes are used to maintain proper image registration in order to allow correction for spectral overlap. The MicroFRET system also utilizes fluorescent protein standards which are reversibly bound to high-performance Sepharose beads.

In addition, newly designed software is capable of displaying processed pixel images of donor, acceptor, and FRET pixel information. Calibration parameters obtained from tagged beads can be applied to other images where the conditions under which the images are acquired are identical. This new design also makes it feasible to detect relatively small amounts of FRET within a given pixel, because the mathematical correction is much simpler (and therefore more accurate) than was previously possible.

Steady-state FRET imaging of cells by sensitized emission, using conventional microscopy, has previously suffered from an inability to correct for spectral overlap while maintaining spatial accuracy. Until now, the three epifluorescence cubes (donor, acceptor and FRET) that must be used to generate the correction values have been manufactured with optical surfaces that are not strictly parallel. This defect created geometric distortions in the image (i.e., displacement of pixels) after the images were combined. The invention utilizes epifluorescence cubes which have been machined to precise tolerances, so that spatial co-registration is maintained for all of the images. The invention also provides beads that are useful as calibration standards, so that spectral overlap can be corrected and features can be identified within the image that display donor emission, acceptor emission, and donor-sensitized acceptor emission (FRET). By subsequently applying an ortho normalization algorithm ("pixel purification"), the pure donor, pure acceptor, and FRET beads are processed as blue, green, and red, respectively. The processing is useful to cell biologists who seek to determine the spatial distribution of each of the three fluorescent components.

Another concern with sensitized emission using conventional microscopy has been that the exciting light can photobleach the donor, thereby reducing the apparent intensity of the FRET signal. However, by utilizing a high sensitivity camera, the sensitized emission technique of the invention does not reduce the FRET signal by more than about 5%.

The invention provides quantitative FRET technology in 3-dimensional imaging systems such as confocal microscopes. Potential applications of quantitative FRET microscopy are almost innumerable and span several disciplines in biology, from basic mechanistic aspects of cell biology to the discovery of new pharmaceuticals.

The device of the invention and improved methods for FRET microscopy will facilitate cell biology experiments involving tagged proteins (e.g., protein-protein interactions) as well as drug discovery (protein-small molecule interactions), where there is a need to quantitate the extent to which two molecules are interacting.

The invention includes bead standards applicable to 3-D imaging, as well as software that calibrates volume elements.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

All publications, patent applications, patents, and other references mentioned herein are incorporated by reference in their entirety. In case of conflict, the present application, including definitions, will control. In addition, the materials and methods described herein are illustrative only and not intended to be limiting. Other features and advantages of the invention will be apparent from the following detailed description, the drawings, and from the claims.

Optical Instrumentation

The methods of the invention use an optical device that acquires spatially co-registered electronic images. For example, the optical instrument can be a microscope and digital camera. The microscope can be a steady-state, wavelength-scanning fluorescence microscope (i.e., not a time-resolved system or not an interferometer-based system). The optical instrument can also provide for background subtraction, spectral overlap corrections, and transformation of data from three channels set into a color space defined by the primary colors of red, green, and blue. The transformation of data produces an enhanced image in which FRET, acceptor, and donor pixels are more clearly differentiated and pseudocolored accordingly.

FIG. 1a is a block diagram showing one embodiment of a FRET imaging microscope for acquiring spatially co-registered electronic images suitable for use with the present invention. The structure includes a microscope 1, a detection camera 2, a light source 3, a set of three interchangeable epifluorescence cubes 4 (donor, acceptor, and FRET), an image processor 5, and an image output device 6.

In a specific embodiment, the MicroFRET instrument is based on an Olympus BX60 (upright) or IX70 (inverted) epifluorescence microscope 1. The detection camera 2 uses a KAIROS Peltier-cooled charge-coupled device (CCD) camera (Model K7: 16 bit, 760×510 resolution, or Model K8: 16 bit, 1340×1037 resolution) coupled to the trinocular port of the microscope 1. The detection camera 2 coupling to the microscope is made through a c-mount to Olympus U-PMTVC and Olympus U-SPT relay tubes (containing a 2.5×projection eyepiece). The threaded U-PMTVC mount can be adjusted to make the detection camera 2 parfocal with the oculars. Other hardware components used in this study include a 10×/0.40 objective (U-plan apo infinity/0.17).

The light source 3 for excitation illumination can be provided by a 75 watt quartz tungsten halogen (QTH) light source coupled directly to the microscope 1, although other light sources may be used if desired. Exposure time is controlled by an electronic shutter in the detection camera 2. Typical exposure times are 0.15–2 seconds. The use of low light doses in imagery was enabled by minimizing exposure time and intensity, using extremely sensitive CCD cameras, and by carefully selecting epifluorescence cubes 4 with broad band emission filters and narrow band excitation filters. Spectral deconvolution algorithms readily correct for the broad-band emission filters.

FIG. 1b is a diagram of an epifluorescence filter cube 4. Each epifluorescence cube 4 includes an excitation filter 10, an emission filter 1, and a dichroic mirror 12. The excitation filter 10 is a band pass or high pass filter that allows only short wavelength light from a light source to pass through. The emission filter 11 is a band pass or low pass filter that passes only long wavelength light emitted by the object in response to illumination by the shorter wavelength exciting light. The dichroic mirror 12 is a beam splitter that reflects the exciting light onto the object and then allows emitted light from the object to pass through. The "cut on" wavelength of the dichroic mirror 12 generally lies between the transmission bands of the excitation filter 10 and the emission filter 11 in a simple configuration.

The methods of the invention use epifluorescence cubes 4 which have been machined to precise tolerances, so that spatial co-registration is maintained for all of the images. This design also makes it feasible to detect relatively small amounts of FRET within a given image pixel, because the mathematical correction is much simpler (and therefore more accurate) than was previously possible. The epifluorescence cubes 4 are precisely milled and fabricated, such that there is less than 5 arc seconds deviation between the two planar surfaces of each of the dichroic mirrors and emission filters in the epifluorescence cubes. This low deviation between the two planar surfaces of each of the dichroic mirrors and emission filters results in a high degree of image registration. Because image registration and distortion are highly dependent on exact surface parallelism within the dichroic and emission filters' surfaces, the dichroic and emission filters of all three cubes were measured for surface parallelism (using an autocollimator) and for surface flatness (using an interferometer) and found to be less than or equal to 15 arc seconds of wedge parallelism and approximately 10 waves flatness. Epifluorescence cubes having suitable characteristics were manufactured by Chroma Inc. (Brattleboro, Vt.) to the specifications of less than 2 waves flatness and 5 arc seconds wedge. Lesser quality epifluorescence cubes can be corrected by optical centering adjustment (OCA) devices (from Olympus of Huntington, N.Y.) in conjunction with donor (D), acceptor (A), and FRET (F) cubes to co-align images in run time using a focusing/alignment acquisition loop implemented in software. The target can be a fluorescent bead (size=point source) visible in all three channels and aligned to one pixel in co-registration among the three channels. This is a novel use of OCA's for FRET. Preferred epifluorescence cube specifications are described in TABLE 1.

TABLE 1

Spectral characteristics of epifluorescence cubes. Wavelengths (nm) are given as cut-on and cut-off (50% peak transmission) for excitation and emission filters, and as the inflection point for dichroic filters.

| Cube/Channel | Excitation | Dichroic | Emission |
|---|---|---|---|
| Donor/$C_1$ | 335–380 | 410 | 435–490 |
| Acceptor/$C_2$ | 450–490 | 495 | 505–550 |
| FRET/$C_1$ | 335–380 | 410 | 505–720 |

The $C_1$ channel (arbitrarily assigned to Blue) was designed to selectively excite and image donor (D) emission, the $C_2$ channel (arbitrarily assigned to Green) was designed to selectively excite and image acceptor (A) emission, and the $C_3$ channel (arbitrarily assigned to Red) was designed to visualize FRET (F) emission, since excitation was at the donor excitation and imaged at the acceptor emission.

Conventional epifluorescence cubes may be replaced by Fluorescence Imaging Micro-Spectrophotometer (FIMS) technology or other methods which do not use a set of three fixed-wavelength devices. In FIMS, the emission filter is continuously variable and the excitation wavelength can be selected by another device, such as a monochromator. A description of the FIMS technology is set forth U.S. patent application No. 08/833,351, filed Feb. 10, 1998, entitled "Optical Instrument Having a Variable Optical Filter", and assigned to the assignee of the present invention.

The image processor 5 may be a suitably programmed personal computer. The image output device 6 may be a computer monitor (e.g., CRT or LCD display) or a printer. In operation, a monochrome image of an illuminated sample is taken by the detection camera 2 through the microscope 1 and input into the processor 5 as a digitized pixel image. A set of three such images from each channel (donor, acceptor, and FRET) can then be processed as three spatially coregistered images or treated as a single image in which each pixel has three color space coordinates corresponding to the monochrome wavelengths.

The method of the invention is not limited to an epifluorescence microscope. Macroscopic lens-based systems could be used in place of the microscope's objectives to achieve FRET detection and quantitation over a macroscopic field of view, such as a microtiter tray or petri dish (in biology), or a solid state device (in materials science).

FRET Physics

The Förster equations, which are the basic equations describing FRET, involve expressions for the energy transfer rate constant ($k_t$), the transfer efficiency (E), the so-called Förster radius or critical distance ($R_o$, in cm), the spectral overlap integral (J ($\lambda$)) and the normalized fluorescence emission spectrum of the donor (f ($\lambda$)):

$$k_t = (R_0/r)^6 (1/\tau_d) \tag{1}$$

$$E = [1 + (r/R_0)^6]^{-1} \tag{2}$$

$$R_0 = [8.79 \times 10^{-25} J(\lambda)\kappa^2 Q_D n^{-4}]^{1/6} \tag{3}$$

$$J(\lambda) = \int f(\lambda)\epsilon_A(\lambda)\lambda^4 d\lambda \tag{4}$$

$$f(\lambda) = F_D(\lambda)d\lambda / \int F_D(\lambda)d\lambda \tag{5}$$

r is the center-to-center distance (in cm) between the donor and acceptor chromophores, $\tau_d$ is the fluorescence lifetime of the donor in the absence of energy transfer, $\kappa^2$ is the dipole-dipole orientation factor, $Q_D$ is the fluorescence quantum yield of the donor in the absence of the acceptor, n is the refractive index of the intervening medium, $F_D(\lambda)$ is the fluorescence emission intensity of the donor at a given wavelength $\lambda$ (in cm), and $\epsilon_A(\lambda)$ is the extinction coefficient of the acceptor chromophore (in $cm^{-1}M^{-1}$). $J(\lambda)$ therefore expresses the normalized fluorescence spectrum of the donor and has units of $M^{-1}cm^3$.

For randomly oriented molecules separated by a distance r, when $r=R_0$, the efficiency of energy transfer is 50%, and the donor fluorescence lifetime is reduced by a factor of 2. Values of Ro are on the order of tens of Ångstroms. FRET efficiencies fall-off at an inverse $6^{th}$ power of distance as normalized by $R_0$. Doubling the distance between donor and acceptor molecules from $R_0$ to $2R_0$ decreases the FRET efficiency from 50% to approximately 1% because of the inverse-$6^{th}$ power dependence: $(0.5)^6$. Thus, FRET is a very useful tool for determining whether two molecules are in close proximity. This is especially true in the case of interacting macromolecules, where molecular radii are similar in size to the actual $R_0$ values of their fluorescent tags.

The extent to which the donor emission is quenched by the acceptor can be used to calculate the FRET efficiency E according to one of Förster's equations:

$$E = \frac{I_D - I_{DA}}{I_D} \tag{6}$$

where $I_D$ and $I_{DA}$ are the fluorescence intensity of the donor in the absence and presence of acceptor, respectively. This is equivalent to determining the concentration of donors performing FRET, divided by the total concentration of donors.

For most cell biologists, a useful measurement is the relationship of E to r within a color-coded image. The invention provides simple models to convert E to the donor-acceptor distance (r).

Correcting Spectral Overlap

Figure 3:
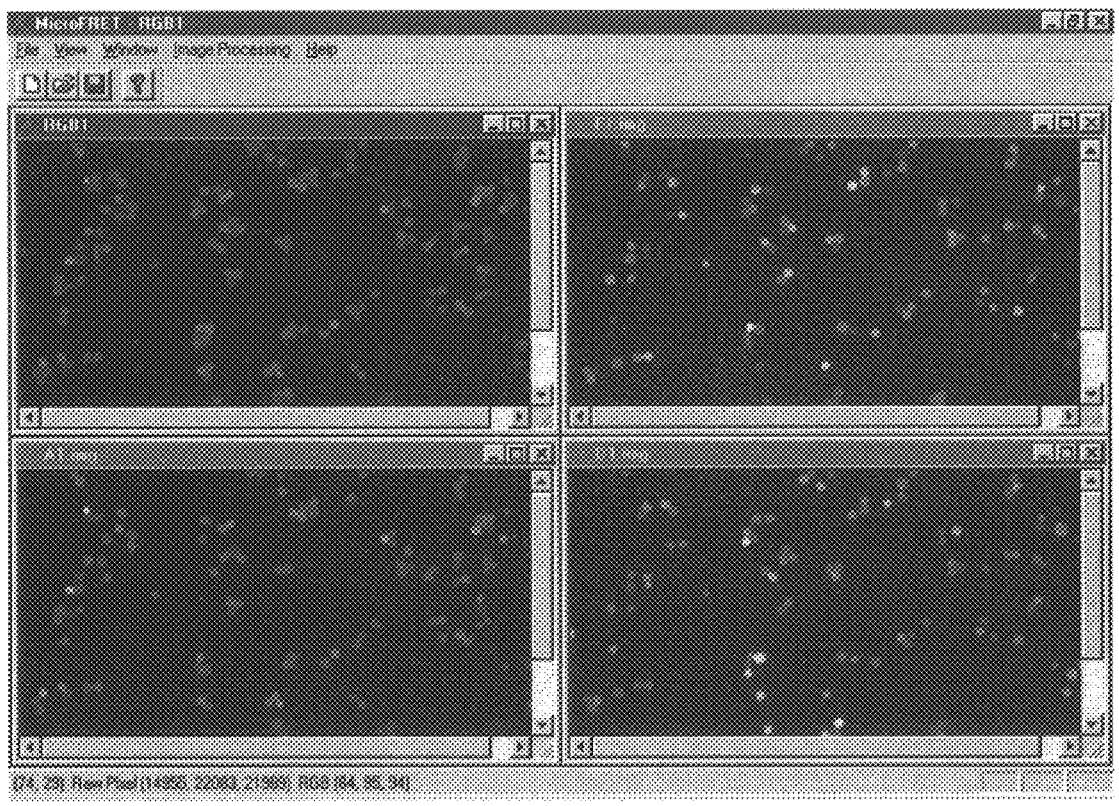
FIG. 3 is an output from a MicroFRET graphical user interface, showing three monochrome images taken of the bead mixture using the donor, acceptor, and FRET epifluorescence cubes described in TABLE 1. These images have been combined to produce an RGB image which does not fully differentiate among the three bead types because of spectral overlap. Windows: lower right ($C_1$); lower left ($C_2$); upper right ($C_3$); upper left (RGB).

In one embodiment, the inventive method corrects for spectral overlap between the donor and acceptor channels (selected excitation and emission wavelength ranges, see supra) The mathematical basis for the spectral overlap corrections is provided as follows:

$$X_u^y \tag{7}$$

where X can be substituted by "D", "A", or "F" to indicate an image pixel from one of the monochrome fluorescence images acquired through the Donor, Acceptor or FRET channels, respectively. The subscript "u", can be substituted by "d", "a" or "f" to represent a pixel from either a donor, acceptor or FRET bead in the image. Since there is substantial spectral overlap, more than one bead type can be seen in each unprocessed channel (FIG. 3). The superscript "y", in the equations (8) and (9) below, is replaced by "b" to indicate that the monochrome image has been background subtracted before spectral overlap corrections are performed.

$F_d^b/D_d^b$=ratio of FRET channel intensity to Donor channel intensity for a "pure donor" pixel after background subtraction on each monochrome image. (8)

$F_a^b/A_a^b$=ratio of FRET channel intensity to Acceptor channel intensity for a "pure acceptor" pixel after background subtraction on each monochrome image. (9)

These ratios are the fractional "bleed" or spectral overlap of donor and acceptor, respectively, into the FRET channel. They are then used to correct the FRET channel pixel intensities. Each pixel in the corrected FRET channel image ($F^c$) is given by:

$$F^c = F^b - (F_d^b/D_d^b) \times - (F_a^b/A_a^b) \times A^b \tag{10}$$

After background and spectral overlap corrected monochrome images are obtained for each channel, the three images are combined into a composite RGB image to create a corrected FRET image. In the illustrated embodiment, the donor channel is not corrected for acceptor bleed and the acceptor channel is not corrected for donor bleed because these effects are minimal.

The correction for spectral overlap is performed as follows: The ratio of the FRET channel intensity to the donor channel intensity is determined for a "pure donor" pixel after background correction. The ratio of the FRET channel intensity to the acceptor channel intensity is also determined for a "pure acceptor" pixel after background correction. These ratios are then used to correct the FRET channel values for each pixel.

Ortho normalization

In one embodiment, the method uses ortho normalization to convert donor, acceptor, and FRET signals into unique colors. For example, the donor, acceptor, and FRET signals are converted to B(lue), G(reen), and R(ed). An ortho normalization procedure which qualitatively enhances the corrected image is described below.

In addition to the spectral overlap algorithm given above, the image can be further enhanced by the construction of RGB images based on an ortho normalization transformation. This process results in the FRET, acceptor, and donor pixels being pseudocolored by pure primary colors: red, green, and blue respectively. To do this, selected pixel values from each of the previously processed monochrome images can be used to construct a 3×3 matrix, referred to as the A matrix:

$$\text{Selected Pixel} \begin{array}{c} \\ f \\ a \\ d \end{array} \begin{array}{c} \text{Monochrome Image} \\ \text{(Grayvalue Image)} \\ \begin{array}{ccc} F & A & D \end{array} \\ \begin{bmatrix} A_{11} & A_{12} & A_{13} \\ A_{21} & A_{22} & A_{23} \\ A_{31} & A_{32} & A_{33} \end{bmatrix} = [A] \end{array} \quad (11)$$

Columns in [A] represent the three previously processed monochrome images and rows represent selected pixels. For example, $A_{11}$ is equal to a pixel value in the FRET image which corresponds to the location of a FRET bead. $A_{12}$ and $A_{13}$ are equal to the pixel value in the acceptor and donor images, respectively, at this same position.

The goal of the ortho normalization operation is to transform the A matrix into the following matrix:

$$\text{Selected Pixel} \begin{array}{c} \\ f \\ a \\ d \end{array} \begin{array}{c} \text{Monochrome Image} \\ \text{(Grayvalue Image)} \\ \begin{array}{ccc} F & A & D \end{array} \\ \begin{bmatrix} C_{11} & 0 & 0 \\ 0 & C_{22} & 0 \\ 0 & 0 & C_{33} \end{bmatrix} = [C] \end{array} \quad (12)$$

Where $C_{11}$, $C_{22}$ and $C_{33}$ are set to the maximum possible pixel value. The transformation can be expressed as follows:

$$[A][B]=[C] \quad (13)$$

Knowing [A] and [C], the B matrix can be determined by multiplying both sides of the equation (13) by the inverse of A:

$$[A]^{-1}[A][B]=[B]=[A]^{-1}[C] \quad (14)$$

The A matrix can be inverted, provided that the selected pixels define independent axes. Once the B matrix has been determined, each RGB pixel value triad is multiplied by the B matrix to determine the new triad. The transformation may cause some gray values to be negative, so their absolute value is always used. The transformation may also cause gray-values to exceed their maximum possible value. Accordingly, all of the new gray values are scaled so that the maximum gray value in the RGB image is equal to the maximum possible grayvalue. This completes the purification process.

In terms of process steps, ortho normalization may be performed by:

(1) Selecting at least two image regions in an initial image, each image region including at least one pixel, wherein the image regions define at least two distinguishable spectral categories.

(2) Performing a color space transformation such as ortho normalization on the initial image, based on the color space coordinates of the pixels in each of the selected image regions, to generate a processed image. (If desired, ortho normalization may be performed serially on a dynamic series of initial images, or a series of acquired digitized images can all be corrected simultaneously).

(3) Evaluating the processed image for a visible indication of an improved spatial distribution of color. The step of evaluating may be based on the improved spatial distribution of colors properly segregating to known standard targets, or the improved spatial distribution of colors segregating to biological structures. Preferably, a confocal microscope is used to perform such evaluation in order to observe three-dimensional spatial information.

The ortho normalization step is useful to cell biologists who may reiteratively select candidate pixels as representatives of the donor, acceptor, and FRET. This human intervention could be a key component in extracting data from images: the quality of the pixel selection would be evaluated by the resulting morphology of the pseudocolored image. For example, if FRET is observed within a particular structure after the spectral overlap correction, it might be advantageous to test various pixels within this structure by re-selecting candidate "red" pixels.

These algorithmic methods (whether involving imaging or not) may be adaptable to flow cytometry (including imaging-in-flow methods) or sorting of cells in a flow system.

Quantitative FRET Measurements

In one embodiment, the quantitative method of the invention performs quantitative FRET measurements and analyses. FRET image data is obtained with standard filter sets in a fluorescence microscope. One set of equations for quantitative FRET is provided below (equations 15a–30). These equations are similar to or derived from FRET correction equations set forth in Gordon, et al., Quantitative Fluorescence Resonance Energy Transfer Measurements Using Fluorescence Microscopy, Biophysical Journal, Vol. 74, May 1998 2702:2713, which is hereby incorporated by reference. The two and three letter symbols used in the equations have the following meanings:

Aa is the signal from an acceptor-only specimen using the acceptor filter set;

Dd is the signal from a donor-only specimen using the donor filter set;

Fa is the signal from an acceptor-only specimen using the FRET filter set;

Fd is the signal from the donor-only specimen using the FRET filter set;

Ad is the signal from a donor-only specimen using the acceptor filter set;

Da is the signal from an acceptor-only specimen using the donor filter set;

Df is the signal from an 'acceptor plus donor' specimen using the donor filter set;

Ff is the signal from the 'acceptor plus donor' specimen using the FRET filter set;

Af is the signal from an 'acceptor plus donor' specimen using the acceptor filter set;

Dfd refers to only the donor signal with the Donor filter set when both donor and acceptor are present;

Dfa refers to only the acceptor signal with the Donor filter set when both donor and acceptor are present;

Ffd refers to only the donor signal with the FRET filter set when both donor and acceptor are present;

Ffa refers to only the acceptor signal with the FRET filter set when both donor and acceptor are present;

Afd refers to only the donor signal with the Acceptor filter set when both donor and acceptor are present;

Afa refers to only the acceptor signal with the Acceptor filter set when both donor and acceptor are present;

$\overline{Dfd}$ refers to the donor signal with the Donor filter set that would have been if no acceptor were present and therefore no FRET occurred;

$\overline{Afa}$ refers to the acceptor signal with the Acceptor filter set that would have been if no donor were present and therefore no FRET occurred.

The FRET symbols used in the following equations have the following meanings:

FRET1 is the loss of donor signal due to FRET using Donor filter set in the method using three-filter sets;

FRETN is the normalized measure of FRET equal to FRET1/($\overline{Dfd} \times \overline{Afa}$);

FRET2 is equal to FRET1/$\overline{Dfd}$;

FRET3 is equal to FRET1/($\overline{Dfd} \times \overline{Afa}$), which equals FRETN;

FRET4 is the loss of donor signal due to FRET using Donor filter set in the method using two-filter sets;

G is the factor relating the loss of donor emission due to FRET in the Donor filter set to the gain of acceptor emission due to FRET in the FRET filter set.

Note that in a two-filter system, the following substitutions may be made:

Dd' is similar to Dd but with acceptor concentration proportional to donor concentration;

Fd' is similar to Fd but with acceptor concentration proportional to donor concentration;

Ad' is similar to Ad but with acceptor concentration proportional to donor concentration;

Da' is similar to Da but with acceptor concentration proportional to donor concentration;

Fa' is similar to Fa but with acceptor concentration proportional to donor concentration;

Aa' is similar to Aa but with acceptor concentration proportional to donor concentration.

Additional corrections for FC can be derived from equations 15a–30 below, where equation (10) is rewritten in the terms defined above as equation (15):

$$F^c = Ff - Df\,(Fd/Dd) - Af\,(Fa/Aa) \tag{15}$$

In particular, $F^c$ can be (1) corrected for cross-talk resulting from detection of donor fluorescence through an acceptor emission channel and/or acceptor fluorescence through a donor emission channel (e.g., corrected for non-zero values of Ad and Da); (2) normalized for the concentration of a donor, preferably by applying a correction of 1/Df; (3) normalized for the concentration of an acceptor, preferably by applying a correction of 1/Af; (4) normalized for the concentration of a donor and an acceptor, preferably by applying a correction of 1/($D_f \times A_f$); (5) corrected for cross-talk and normalized. In addition, the initial FRET image is improved with respect to photobleaching by using a sensitive camera and fast exposure times.

$$Df = Dfd + Dfa \tag{15a}$$

$$Ff = Ffd + Ffa \tag{15b}$$

$$Af = Afd + Afa \tag{15c}$$

$$Df = Dfd + Ffa(Da/Fa) \tag{16a}$$

$$Ff = Dfd(Fd/Dd) + Ffa \tag{16b}$$

$$Af = Dfd(Ad/Dd) + Afa \tag{16c}$$

$$Dfd = \overline{Dfd} - FRET1 \tag{17}$$

$$Afa = \overline{Afa} + G \cdot FRET1(Ad/Fd) \tag{18a}$$

$$G = \frac{QY_a}{QY_d}\frac{\phi_a}{\phi_d}\frac{T_F}{T_D} \tag{18b}$$

$$Ffa = \overline{Afa}(Fa/Aa) + G \cdot FRET1 \tag{19}$$

$$Dfa = \overline{Afa}(Da/Aa) + G \cdot FRET1(Da/Fa) \tag{20}$$

$$Df = \overline{Dfd} - FRET1 + \overline{Afa}(Da/Aa) + G \cdot FRET1(Da/Fa) \tag{21a}$$

$$Ff = (\overline{Dfd} - FRET1)(Fd/Dd) + \overline{Afa}(Fa/Aa) + G \cdot FRET1 \tag{21b}$$

$$Af = (\overline{Dfd} - FRET1)(Ad/Dd) + \overline{Afa} + G \cdot FRET1(Ad/Fd) \tag{21c}$$

$$\overline{Afa} = \frac{Af - (Ad/Fd)Ff}{1 - (Fa/Aa)(Ad/Fd)} \tag{22a}$$

$$FRET1 = \frac{Ff - (Fd/Dd)Df - \overline{Afa}[(Fa/Aa) - (Fd/Dd)(Da/Aa)]}{G[1 - (Da/Fa)(Fd/Dd)]} \tag{22b}$$

$$\overline{Dfd} = Df + FRET1[1 - G(Da/Aa)] - \overline{Afa}(Da/Aa) \tag{22c}$$

$$FRETN = \frac{FRET1}{\overline{Dfd} \cdot \overline{Afa}} \propto \frac{[\text{bound}]}{[\text{total } d] \cdot [\text{total } a]} \tag{23}$$

$$K_{eq} = [\text{bound}]/([\text{free } d] \cdot [\text{free } a]) \tag{24}$$

$$FRETN = \frac{Ff - Df(Fd/Dd) - Af(Fa/Aa)}{G \cdot Df \cdot Af} \tag{25}$$

$$Df = \overline{Dfd} - \overline{Dfd} \cdot FRET2 + \overline{Afa}(Da/Aa) + G \cdot \overline{Dfd} \cdot FRET2(Da/Fa) \tag{26a}$$

$$Ff = (\overline{Dfd} - \overline{Dfd} \cdot FRET2)(Fd/Dd) + \overline{Afa}(Fa/Aa) + G \cdot \overline{Dfd} \cdot FRET2 \tag{26b}$$

$$Af = (\overline{Dfd} - \overline{Dfd} \cdot FRET2)(Ad/Dd) + \overline{Afa} + G \cdot \overline{Dfd} \cdot FRET2(Ad/Fd) \tag{26c}$$

$$\overline{Afa} = \frac{Af - (Ad/Fd)Ff}{1 - [(Ad/Fd)(Fa/Aa)]} \tag{27a}$$

$$FRET2 = \frac{Ff - (Fd/Dd)Df - \overline{Afa}[(Fa/Aa) - (Fd/Dd)(Da/Aa)]}{Ff[1 - (Da/Fa)G] - Df[(Fd/Dd) - G] - \overline{Afa}[(Fa/Aa) - (Fd/Dd)(Da/Aa)]} \tag{27b}$$

$$FRETN = FRET2/\overline{Afa} \tag{28}$$

-continued $$Df = \overline{Dfd} - \overline{Dfd} \cdot \overline{Afa} \cdot FRET3 + \overline{Afa}(Da/Aa) + \quad (29a)$$
$$G \cdot \overline{Dfa} \cdot \overline{Afa} \cdot FRET3(Da/Fa)$$

$$Ff = (\overline{Dfd} - \overline{Dfd} \cdot \overline{Afa} \cdot FRET3)(Fd/Dd) + \quad (29b)$$
$$\overline{Afa}(Fa/Aa) + G \cdot \overline{Dfd} \cdot \overline{Afa} \cdot FRET3$$

$$Af = (\overline{Dfd} - \overline{Dfd} \cdot \overline{Afa} \cdot FRET3)(Ad/Dd) + \quad (29c)$$
$$\overline{Afa} + G \cdot \overline{Dfd} \cdot \overline{Afa} \cdot FRET3(Ad/Fd)$$

$$FRETN = FRET3 = FRET2/\overline{Afa} = FRET1/(\overline{Dfd} \cdot \overline{Afa}) \quad (30)$$

FRET Beads as Calibration Standards

The invention provides a set of calibration targets, including a variety of "FRET Beads" applicable to widely-used FRET pairs. The invention also provides a method for imaging the FRET standards in a conventional three-channel (i.e., three-cube) epifluorescence microscope, and applying FRET calibration algorithms such that donor concentration [D], acceptor concentration [A], and FRET efficiency (E) values can be determined on unknown samples. An advantage of using surfaces such as beads as FRET calibrants, rather than solution-based techniques, is that the use of surfaces such as beads eliminates unwanted interference by various physico-chemical phenomena, such as singlet-singlet annihilation. Other effects may accentuate FRET on surfaces as excitons are formed.

In one embodiment, the invention provides FRET Beads with His-tagged GFP derivatives to Ni/NTA derivatized Sepharose beads at a surface concentration that is sufficiently high to achieve efficient FRET between donor and acceptor molecules, e.g., between blue-emitting (BFP) and green-emitting GFP derivatives. These FRET Beads provide a surface to associate (bind) these His-tagged proteins very tightly in aqueous solution (stable for months at 4° C.); however, protein dissociation and release from the bead can be accomplished immediately by the addition of imidazole. Release from the bead modulates the FRET properties of donor and acceptor molecules (i.e., FRET efficiency goes to zero). This treatment can be performed in the same fluorimeter cuvette; the difference in spectra taken before and after release is a direct indication of FRET efficiency. Previously, FRET parameters were extremely difficult to obtain; for example, artifacts can be generated by alternative procedures such as loading highly concentrated donor and acceptor solutions into microcapillaries. The invention of a FRET Bead with selective release makes these parameters trivial to measure. The simple procedure of adding 1 M imidazole enables accurate determination of donor and acceptor concentrations and efficiency, thereby furnishing the basis for calibration standards in quantitative FRET microscopy. These calibrated beads are used to determine instrument response and to standardize the epifluorescence microscope hardware and software for use with a variety of samples.

In one embodiment, the invention provides a series of FRET Beads bearing derivatives of the Green Fluorescent Protein that are of current interest to cell biology. These include a blue/green pair (380 nm excitation/s 10 nm emission) and a cyan/"yellow" pair (450 nm excitation/530 nm emission).

Figure 2:
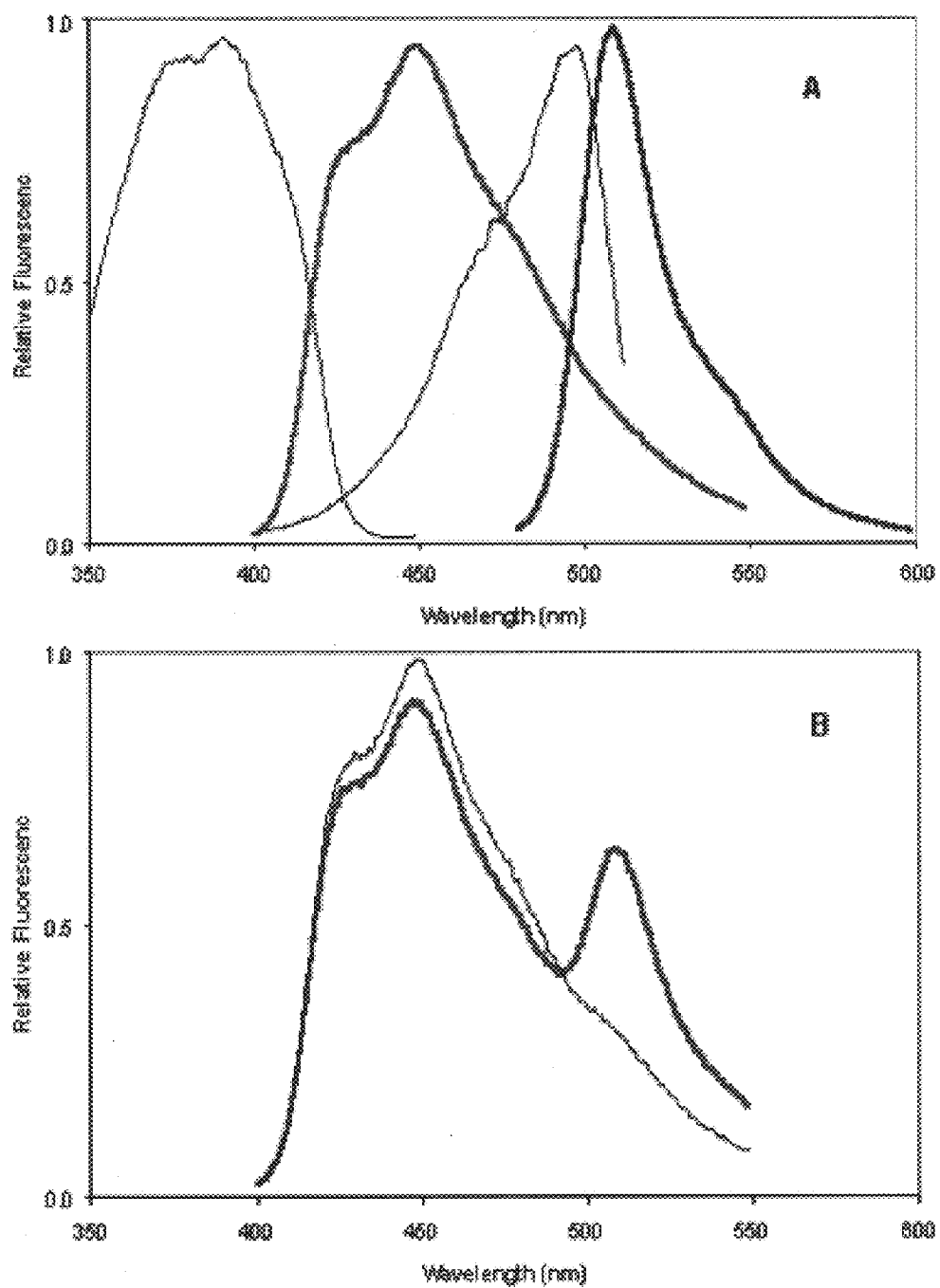
FIG. 2, panel A shows the fluorescence excitation (thin lines) and emission (thick lines) spectra of BFP11 (blue) and RSGFP4 (green) proteins attached to chelating Sepharose beads via their His tags. Panel B is a comparison between the fluorescence emission of the BFP11 and RSGFP4 FRET pair bound (thick line) and following release (thin line) from chelating beads.

Two derivatives of GFP are used for FRET standards, based on their spectral properties. The mutant BFP11, constructed by Lossau et al. (*Chem. Physics.* 213: 1–16, 1996) using combinatorial mutagenesis, contains the mutations F64M/Y66H. BFP11 has blue-shifted excitation and emission maxima relative to wild-type GFP (FIG. 2). The mutant RSGFP4 (Delagrave et al., *Bio/Technology*, 13:151–154, 1995), generated by combinatorial mutagenesis, contains the mutations F64M/S65G/Q69L. RSGFP4 has spectral properties similar to the S65T mutant reported by Heim et al. (*Proc. Natl. Acad. Sci. USA* 91:12501–12504, 1994). As the acceptor in a FRET pair, both S65T and RSGFP4 are superior to other red-shifted excitation mutants such as RSGFP8 (F64L+S65T), because the latter mutant has significant excitation in the violet.

Calibration values can be stored on a computer for future normalization and correction of samples that do not include calibration standards (i.e., pure donor, acceptor, or FRET Beads) in the same field of view. Once calibrated for a particular pair of fluorophores matched to a specific set of cubes within a defined optical bench, these normalization factors are stable and applicable to unknowns containing these fluorophores.

FRET Beads provide a vehicle enabling one to relate a measured intensity of acceptor fluorescence sensitization to a corresponding amount of donor quenching. This calibration factor, $X_F$, embodies not only instrument response but also the concept of a FRET quantum yield. $X_F$ greatly simplifies the determination of the amount of donor performing FRET without the need to photodestruct or otherwise physically separate donor from acceptor. This calibration factor also compensates for differences in absorption cross-sections, excitation intensities, and detection efficiencies.

By combining the E value determined by conventional fluorimetry measurements of E and quantitative imaging, $X_F$ is derived from a FRET calibration bead:

$$X_F = \frac{C_3'}{C_1}\left(\frac{1-E}{E}\right)X_D \quad (34)$$

where $C_1$ is the intensity from the $C_1$ channel and $C_3'$ is the intensity from the $C_3$ FRET channel after spectral overlap corrections have been made using equation (38), below.

This value can then be applied to the calculation of FRET parameters in sample unknowns. From equation (6), E is equivalent to determining the number of donors performing FRET, divided by the total number of donors. Since the Forster equations apply to a single donoracceptor pair, the amount of donors performing FRET can be directly related to the measured sensitized acceptor emission. In the three-cube microscope system, E of FRET samples can be determined by incorporating the bead calibration factors ($X_D$ and $X_F$) and combining the $C_1$ and $C_3$ channel information as:

$$E = \frac{H_3'}{H_1 + H_3'} \quad (35)$$

where $H_3' = \frac{C_3'}{X_F}$ and $H_1 = \frac{C_1}{X_D}$ respectively.

Thus equations (34) and (35), used in conjunction with FRET Beads, greatly facilitate the conversion of sensitized acceptor emission into units compatible with quenched donor emission, resulting in the ability to readily quantitate the amount of donor performing FRET, the total amount of donor, and the FRET efficiency.

Figure 8:
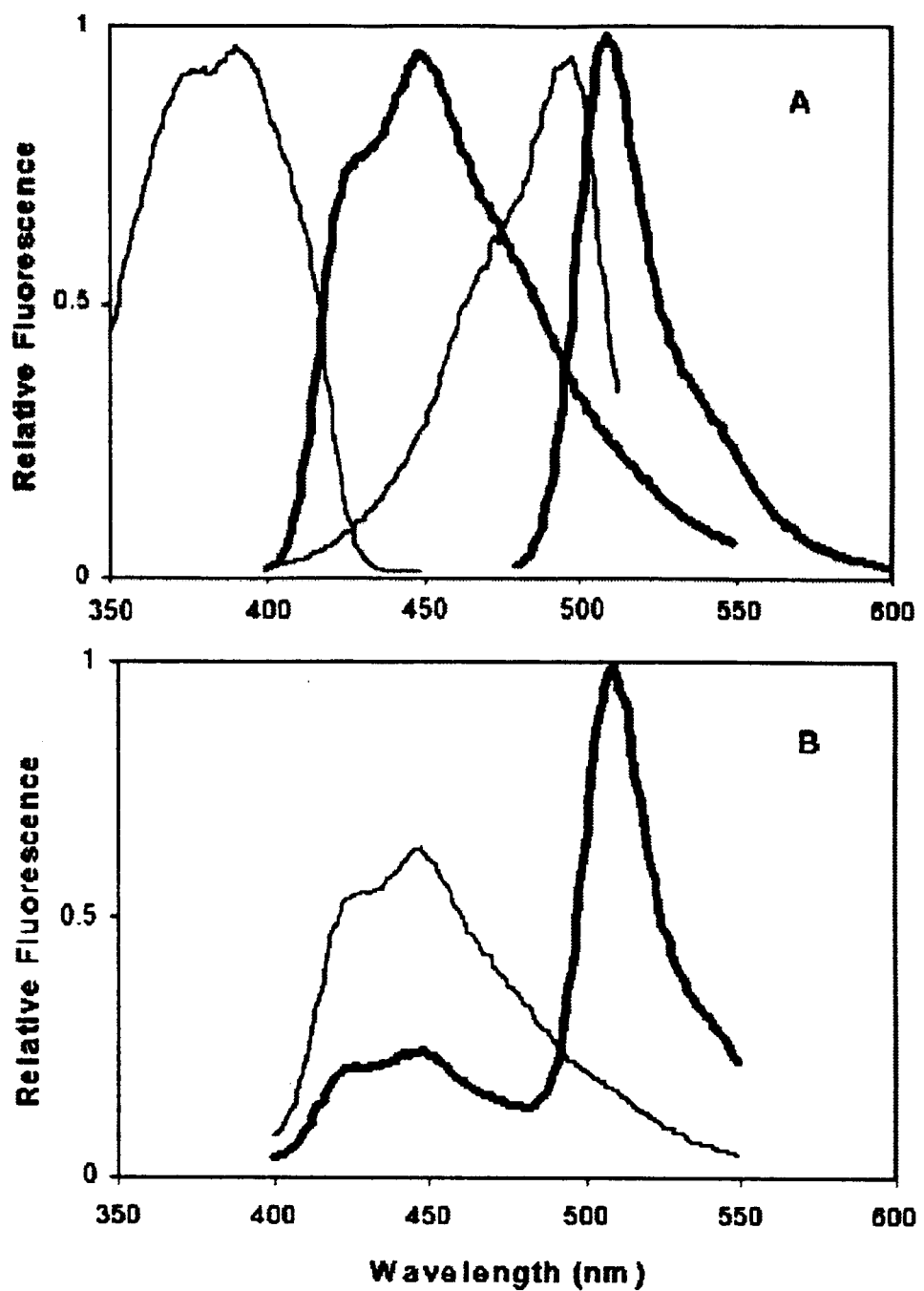
FIG. 8, panel A shows the fluorescence excitation (thin lines) and emission (thick lines) spectra of a blue (BFP 11) and a green (RSGFP4) GFP derivative chelated to Ni/NTA Sepharose beads via the proteins' His-tags. These spectra are virtually indistinguishable from those of the corresponding purified proteins in solution. Panel B is a comparison between the fluorescence emission (with excitation at the donor's wavelength, 370 nm) of the BFP11/RSGFP4 FRET pair bound to the bead (thick line) and following release (thin line) by treatment with imidazole. The spectra shown in FIG. 8 confirm that the fluorescence emission from the FRET Bead is due to energy transfer, and that the spectral properties of the two GFP variants have not changed as a result of binding to the Ni/NTA Sepharose beads.

For the beads shown in FIG. 8, from the y-axis values, $I_D$=0.63 and $I_{DA}$=0.24. The energy transfer efficiency E is determined by substituting into equation (6):

$$E = \frac{0.63 - 0.24}{0.63} = 0.62 \text{ (i.e., 62\% efficient in energy transfer)}$$

Measurement of E enables the mean separation distance (r) between donor and acceptor to be calculated using another one of the Förster equations:

$$r = R_0 \left(\frac{1-E}{E}\right)^{1/6} \tag{36}$$

where $R_0$ is the Förster radius or critical distance at which the efficiency of energy transfer is 50%. $R_0$ can be determined using semiempirical methods and the following (see, equation (3)):

$$R_0 = [8.79 \times 10^{-25} \, J(\lambda) \kappa^2 Q_D n^{-4}]^{1/6} \tag{37}$$

Parameters in equation (37) include J, the spectral overlap integral, which is graphically equivalent to the integrated area shared between the donor's fluorescence emission spectrum and the acceptor's ground state absorption spectrum, both normalized to unity. Other parameters include: $Q_D$, the fluorescence quantum yield of the donor in the absence of acceptor; n, the index of refraction, which for a cellular system is typically (1.3×1.4); $\kappa^2$, the dipole-dipole orientation factor. Considering the spectral overlap for the BFP11/RSGFP4 pair shown in FIG. 8, and random orientation factors, $R_0$ is approximately 40 Å. Substitution of $R_0$ and E into equation (36) results in a separation distance r of 37 Å between BFP11 and RSGFP4 on the FRET Beads described above. This BFP11-RSGFP4 distance is reasonable considering that the minimum possible distance between the fluorophores is ~25 Å, as indicated by the X-ray structure of the GFP dimer.

The invention also provides a method to characterize (by conventional fluorimetry) a series of beads with controlled quantities of donor and acceptor molecules per unit surface area so as to generate standards with respect to donor concentration [D], acceptor concentration [A], and FRET efficiency (E). The determination of donor intensities in the presence ($I_{DA}$) and absence ($I_D$) of FRET, which are normalized for donor concentrations, is one of the major difficulties in performing quantitative FRET on biological samples. Imidazole mediates the release of the GFP fluorophores from the Ni/NTA-chelating bead to achieve this in essentially one step.

The existence of spectral overlap is noted by observing that each of the monoclrome images shows more than one bead type. In the $C_3$ channel, spectral overlap is a result of bleed-through of the donor's emission tail into the acceptor emission band. In addition, direct excitation of the acceptor can occur at certain wavelengths (e.g., 370 nm) due to a small amount of acceptor absorbance at such wavelengths. Spectral corrections for the $C_3$ channel can be made by adapting equation (10) as follows:

$$C_3^1 = C_3 - (C_3^D/C_1^D) \times C_1 - (C_3^A/C_2^A) \times C_2 \tag{38}$$

where $C_3^D/C_1^D$=the ratio of the FRET channel intensity to the Donor channel intensity for a "pure donor" pixel after background subtraction on each monochrome image, and $C_3^A/C_2^A$=the ratio of the FRET channel intensity to the Acceptor channel intensity for a "pure acceptor" pixel after background subtraction on each monochrome image.

Having derived the fluorophore surface concentrations from solution measurements (see, equation (40)), donor surface concentrations can be related to the donor emission intensity in $C_1$ images of pure donor beads via the following equation:

$$C_1^D = X_D[D] \tag{39}$$

where $X_D$ is defined as the donor calibration factor and has units of grayvalue per molecule per unit area. Likewise, the acceptor calibration factor, $X_A$, can be determined from pure acceptor beads imaged through the $C_2$ channel. Since a three dimensional fluorophore-coated bead is projected onto a two-dimensional imaging surface, care must be taken in selecting pixels to be used for intensity (grayscale) measurements. Given the size and optical density of these beads, it is reasonable to base intensities on the center pixels of each bead and divide by a factor of 2. This is because looking down on a bead in the microscope, fluorescence (which is isotropic) is seen from both the bottom and the top of the bead surface due to the 3D to 2D projection. In determining $X_A$ and $X_D$ it is important to note that the fluorescence quantum yield and instrument response corrections are all embodied within this calibration factor. By constructing and characterizing a series of beads, the linearity of this relationship or the limits of the linear range are determined.

By calibrating the instrument, other factors that influence FRET intensity can be experimentally determined, e.g., the interchromophore separation (r), the orientation factor ($\kappa^2$), and the FRET efficiency (E). These calibrations may enable the user to create images in which the magnitude and spatial distribution of these coefficients are displayed. Values for the first two variables could be determined by adding, for example, corrections for differences in absorption cross section between donor and acceptor, and corrections for differences in excitation intensity and detector efficiency. Values for $K^2$ can be determined by using calibration standards containing chromophores with fixed orientations.

Calibration and Test Samples

In a typical analysis, three images using $C_1$, $C_2$, and $C_3$ are obtained for a calibration slide bearing a mixture of pure donor, pure acceptor, and FRET beads. Fluorescent beads are air-dried on the surface of a microscope slide for imaging. All images recorded used light-minus-dark subtraction to correct for a pedestal of dark counts. The calibration slide is then used to obtain the background-subtracted, spectral overlap correction ratios as well as $X_A$, $X_D$, and $X_F$. After these measurements are made, this slide is removed and replaced with a test sample from which three additional images are obtained under identical experiment conditions. Each of these monochrome images is background subtracted and the overlap corrections applied. The image-based microscope system performs massively parallel analysis on every pixel in the scene. For a 1000×1000 resolution image, this is equivalent to $10^6$ simultaneous single spot measurements. Each pixel can be processed to generate energy transfer efficiency according to equation (35) and distance distribution images according to equation (36), provided that $R_0$ is known. [A] images can be determined from the ratio of the $C_2$ channel to $X_A$, and [D] images can also be derived.

Once the microscope is calibrated for a specific FRET pair, the system remains calibrated for all other samples containing those types of fluorophores. Recalibration is required only if the microscope's hardware is altered (e.g., changing an epi-cube) or if a different FRET pair is studied.

Quantitation of FRET signals can be achieved by correlating measurements made in the MicroFRET device on beads or other targets with conventional measurements made in a fluorimeter. For example, imidazole release of fluorophores from the beads within a cuvette can be used to quantify total donor and acceptor, as described in EXAMPLE 2.

Computer Implementation

The MicroFRET system provides digital imaging spectroscopy (DIS) software that supports algebraic manipulation of images for correcting bleed-through of donor emission into the acceptor channel and for correcting excitation of the acceptor at the donor excitation wavelength, as well as for creating a new RGB axis-set to highlight donor, acceptor, and FRET pixels. The system also provides image processing and display for both 16-bit monochrome images and 24-bit RGB images.

Figure 4:
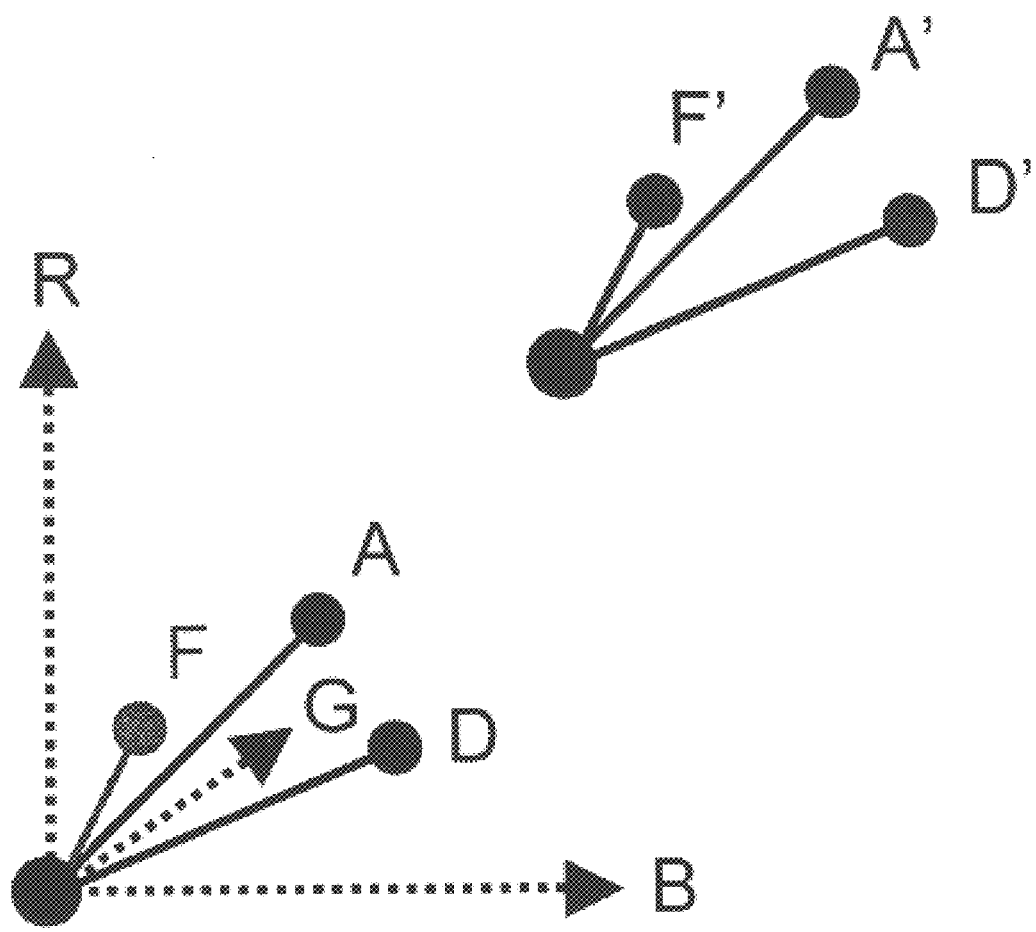
FIG. 4 is an ortho normalization of the color axes for a red-green-blue (RGB) display. This color-correction algorithm redefines the color axes from the dotted arrows of a conventional RGB display (lower left) to the solid axes of the orthonormalized image (upper right). This process results in the primary colors (red, green, blue) being assigned to the three pixel or bead types (FRET, Acceptor, Donor), respectively. Thus, the poorly differentiated colors of the raw RGB image shown in FIG. 3 (F, A, and D) are transformed by ortho normalization into pure red (F'), green (A'), and blue (D').

Correction for spectral overlap was performed as follows: The ratio of the FRET channel intensity to the donor channel intensity is determined for a "pure donor" pixel after background correction. The ratio of the FRET channel intensity to the acceptor channel intensity is also determined for a "pure acceptor" pixel after background correction. These ratios are then used to correct the FRET channel values using equation (10) for each pixel. After a grayvalue image has been obtained for each of the three channels, the three measurements are reassembled into a composite RGB image. However, even though the correction factors for spectral overlap have been calculated for each of the three channels, the various donor, acceptor and FRET beads do not necessarily appear as pure blue, green and red, respectively, because the colors displayed in the initial RGB image have not yet been orthonormalized. MicroFRET allows the user to correct this problem by permitting a user to select pixels that contain the most red, green and blue from the overlap-corrected RGB image. The program mathematically transforms the image to a color system in which the red, green and blue axes are defined by the red, green and blue gray values for the pixels that have been selected (FIG. 4).

Figure 5:
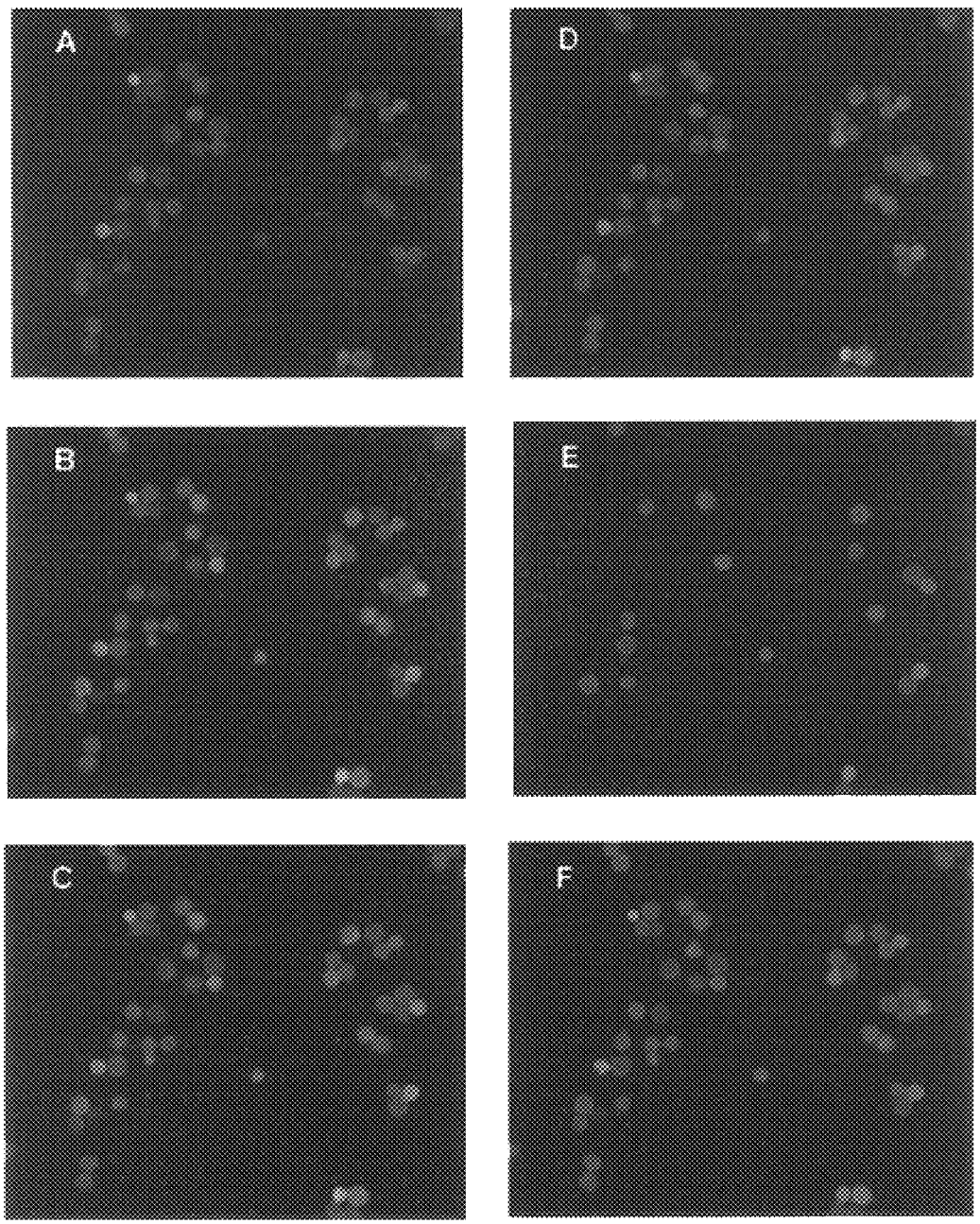
FIG. 5 shows the spectral overlap correction and ortho normalization of donor, acceptor, and FRET beads.

More particularly, the algorithm that is used in MicroFRET transforms an RGB image from the red, green and blue color system into a color system defined by three user-defined RGB triads. A composite RGB image has already been described in FIG. 3, and reproduced as panel A in FIG. 5. The FIG. 5 panels are magnified so that only the upper left quadrant of the FIG. 3 image is shown. Steps in the bleed correction and the ortho normalization of the uncorrected RGB image shown in FIG. 5 (panels A–F) proceed as follows:

Panel 5A—RGB. The monochrome images from FIG. 3 were combined to generate panel 5A using images shown in windows D1, A1, and F1 for the blue, green, and red channels, respectively. The color intensity range for all three color channels is based on the minimum and maximum pixel values of the combined three-image set.

Panel 5B—Scaling corrections. Fluorescence signal intensities among the three channels can vary due to quantum yield and extinction coefficient differences between donor and acceptor. Signal strength is also dependent on instrument parameters such as illumination intensities of the light source and detector sensitivity at different wavelengths. If the range of pixel values differs significantly between channels, the color of the channel with the highest pixel value readings can overwhelm the color of the channel with lower pixel value readings. Panel 5B shows the pseudocolor image after individually rescaling the color intensity of each of the three channels to its minimum and maximum pixel values.

Panel 5C—Background correction. Panel 5C shows the pseudocolor image after each pixel has been corrected for background signals. MicroFRET software prompts the user to select the position of five background pixels by clicking on the image. These pixel values are averaged and automatically subtracted. If any of the subtracted values are negative, they are set to zero.

Panel 5D—Spectral overlap corrections. The data represented in FIG. 3 showed that there is significant spectral overlap among the epifluorescence images. However, because the epifluorescence cubes in the MicroFRET instrument maintain precise image registration, the contaminating contributions to the FRET image (and the other images) can be subtracted from all of the pixels. For the FRET channel, this correction is performed according to equation (10) which minimizes donor and acceptor bead pixel values in the FRET channel so that they approach zero. Only pixels from beads performing FRET maintain significant signal intensity in this channel (red) after correction. Panel 5D shows the pseudocolored image after this overlap correction. The "red contribution" from the pure donor and pure acceptor beads has been removed. The donor beads now appear blue instead of purple and the acceptor beads now appear as green.

Panel 5E—Highlighting FRET. To further demonstrate the correction for spectral overlap, the green and blue channels are turned off in the bleed-corrected image. This simplifies the identification of the "red" pixels where FRET is taking place. This process is easily performed in real-time using a simple tabbed dialog box in which each tab allows the user to selectively contrast enhance a particular channel. As can be seen in panel 5E, only red beads corresponding to FRET are observed.

Panel 5F. Ortho normalization. To enable identification of areas in the sample which contain donor, acceptor, or FRET emission, the software can pseudocolor the image based on user-defined criteria. By clicking the computer mouse on pixels representing each of the three types of beads (i.e., donor, acceptor, and FRET) in panel 5D, the user can reset the color assignments to display corrected emission from the donor to pure blue, the acceptor to pure green, and FRET to pure red (panel 5F).

Computer implementation of this aspect of the invention can be summarized as follows:

1. Select 3 epifluorescence cubes optimized for Donor, Acceptor, and FRET channels.
2. Optically align cubes to within 1 pixel resolution; if using OCA devices, apply run-time software acquisition loop to fluorescent bead visible in all three channels to achieve alignment.
3. Combine images acquired through the three cubes into one RGB image.
4. Either skip to step 9 or perform steps 5–8.
5. Orthonormalize the RGB image by selecting pixels representative of donor, acceptor, and FRET pixels.
6. Repeat step 5 if choice of candidate pixels yields poor mapping of color to either biological morphology or standards.
7. Optionally, save ortho normalization template for application to subsequent images.
8. Contrast enhance R, G, and B in the orthonormalized RGB image. END.
9. Correct the RGB image for background.
10. Further correct for spectral overlap according to equations related to $F^c$.

11. Contrast enhance R, G, and B in the corrected RGB image.

12. Optionally, perform steps 5,6,7,8.

Aspects of the invention may be implemented in hardware or software, or a combination of both. However, preferably, the algorithms and processes of the invention are implemented in one or more computer programs executing on programmable computers each comprising at least one processor, at least one data storage system (including volatile and non-volatile memory and/or storage elements), at least one input device, and at least one output device. Program code is applied to input data to perform the functions described herein and generate output information. The output information is applied to one or more output devices, in known fashion.

Each program may be implemented in any desired computer language (including machine, assembly, high level procedural, or object oriented programming languages) to communicate with a computer system. In any case, the language may be a compiled or interpreted language.

Each such computer program is preferably stored on a storage media or device (e.g., ROM, CD-ROM, tape, or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

EXAMPLES

The capabilities of the MicroFRET device are demonstrated in the EXAMPLES by employing a pair of two widely used fluorescent protein tags. A wider range of applications for this instrument in cell biology studies are possible as more GFP variants with shifted excitation and emission spectra are constructed. Other fluorescent molecules and fluorophores besides GFP derivatives can be analyzed in this instrument by simply choosing an appropriate set of epifluorescence cubes, wherein the donor, acceptor and FRET cubes are designed to separate these signals based on their excitation and emission spectra. Furthermore, this system could also be used with non-protein chromophores such as organic dyes or lanthanide metals, or with combinations of all of these types.

The technique of specific fluorophore-to-bead coupling can be extended to include other chemistries that do not rely on agarose beads, His-tagging, nickel derivatization, or fluorescent proteins. Thus, the beads can have two organic molecules acting as the FRET pair (e.g., fluorescein and rhodamine) while maintaining the ability to selectively release the fluorophores into solution.

Accordingly, the following EXAMPLES are illustrative and are not intended to limit the scope of the present invention.

Example 1

Flourescent Proteins and Beads

This EXAMPLE outlines a procedure to fabricate FRET calibration standards. This involved the synthesis of three types of beads: pure donor; pure acceptor; and FRET beads bearing both donor and acceptor molecules. Each bead type was synthesized as a series, where the values of [D], [A], and E were varied. To construct this series of beads, a Ni/NTA-competitive binder ("S", for spacer) that is His-tagged and has a similar size and shape as the donor and the acceptor was used. In the case of GFP derivatives, several nonfluorescent mutants have been engineered which exhibit a "null" fluorescence phenotype, but nonetheless express large quantities of protein deficient in chromophore (e.g., point mutation R96M). Such His-tagged derivatives make excellent spacers on the surface of the Ni/NTA beads amongst other spectrally active GFP derivatives. The beads can be loaded with protein solutions systematically varied in D, A, and S.

GFP-adsorbed bead standards were prepared using the following procedure. To facilitate protein purification and later attachment on Ni-Sepharose beads, BFP11, RSGFP4, and the R96M variant were engineered to include $His_6$ tags on their amino-termini. The mutant BFP11, constructed using combinatorial mutagenesis, contains the mutations F64M/Y66H (Lossau et al., *Chem. Physics*. 213:1–16, 1996) and is similar to the mutant of Heim et al. (*Proc. Natl. Acad. Sci. USA* 91:12501–12504, 1994). It has blue-shifted excitation and emission maxima relative to wild-type GFP (FIG. 2 and TABLE 2 infra). The mutant RSGFP4, generated by combinatorial mutagenesis by Delagrave et al. (*Bio/Technology*, 13:151–154, 1995), contained the mutations F64M/S65G/Q69L. RSGFP4 has spectral properties similar to the S65T mutant also reported by Heim et al. (*Proc. Natl. Acad. Sci. USA* 91:12501–12504, 1994). As the acceptor in a FRET pair, both S65T and RSGFP4 are superior to other red-shifted excitation mutants such as RSGFP8 (F64L+S65T), because the latter mutant has significant excitation in the violet.

The proteins were expressed in *E. coli* strain BL21(DE3), grown for 24 hours, ruptured in a French press, applied to a Novagen HisBind purification column, eluted in 1 M imidazole, and dialyzed. The final protein concentration was determined by a Bradford assay (Bio-Rad). An SDS-PAGE gel was run to confirm the purity and size of the dialyzed fraction (data not shown). Fluorescence excitation and emission spectra were recorded on a Photon Technology QM-1 fluorimeter.

HiTrap metal chelating Sepharose beads are charged according to the manufacturer's (Pharmacia Biotech) instructions by washing the beads with 50 mM $NiSO_4$. The beads are then washed extensively with 50 mM Tris-HCl (pH 8.0) to remove traces of uncomplexed nickel ions. A solution is made of purified proteins at a total protein concentration of approximately 0.4 mg $ml^{-1}$ in 50 mM Tris-HCl buffer. This dilute concentration is used to avoid GFP dimer formation in solution. 1.5 ml of this mixture is added to 50 $\mu$l of a bead slurry and incubated on ice for 1 hour with frequent mixing. Excess protein ensures that the beads are fully loaded. To remove nonspecifically bound protein (if any) the suspension is washed twice with a buffer containing 5 mM imidazole, 0.5 M NaCl and 20 mM Tris-HCl, followed by one wash with 50 mM Tris-HCl. All washes are done by centrifuging the beads at 1,000×g for 30 secs. in a microcentrifuge and resuspending the pellet in the appropriate buffer. The mean particle size of the beads is approximately 34 $\mu$m.

Figure 6:
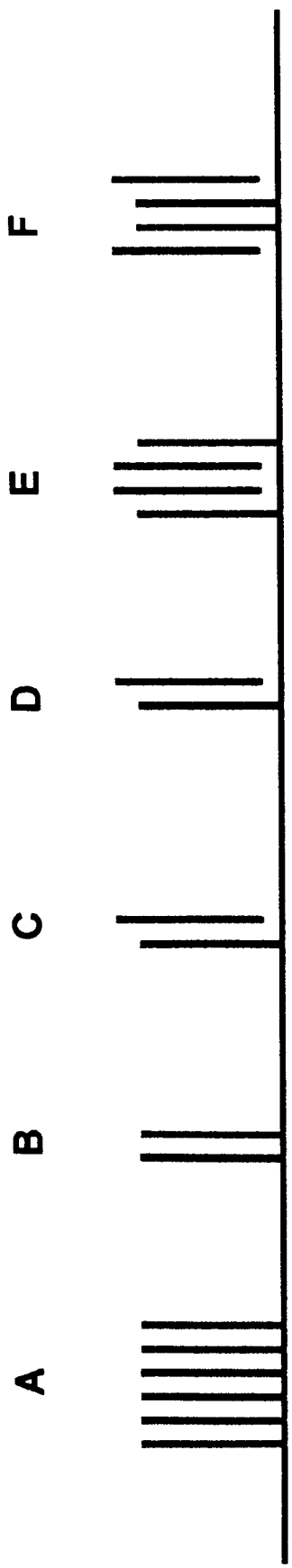
FIG. 6 shows the surface of the chelating bead, as represented by a horizontal black line, with GFP donors and acceptors (e.g., BFP and RSGFP) shown as blue and green vertical lines, respectively. Six different types of possible interactions are labeled A–F. In this drawing, only adjacent molecules are considered to be within an efficient FRET distance.

FIG. 6 shows the surface of the chelating bead, as represented by a horizontal black line, with GFP donors and acceptors (e.g., BFP and RSGFP) shown as blue and green vertical lines, respectively. Six different types of possible interactions are labeled A–F. In this drawing, only adjacent molecules are considered to be within an efficient FRET distance.

The most heavily loaded beads were produced (under saturating conditions) to have optical densities under 0.1; therefore, photon-mediated trivial energy transfer or reabsorption do not have to be considered. In addition, the bead size is sufficiently large that surface resonance effects can be ignored.

Example 2

Conventional Flourimetry on the GFP-Labeled Fret Beads

To confirm that the fluorescence emission from the FRET bead is actually FRET, as well as to ensure that the spectral properties of the two GFP variants have not changed as a result of binding to the Sepharose beads, a sample of each type of bead was treated with imidazole, which releases the protein. Fluorescence emission spectra for the FRET beads are shown in FIG. 2 and 8. The thick line of the B panels shows the emission spectrum of a suspension of FRET beads excited at 370 nm. The thin line of the B panels shows the emission spectrum of the same beads after both RSGFP8 and BFP-11 have been released from the beads by treatment with imidazole. The decreased donor emission and enhanced acceptor emission are characteristic of FRET. This effect is reversed when the two proteins are released from the beads.

To determine [D] and [A] for each bead in a series, the concentrations of donor and acceptor were first measured in solution after release by treating with imidazole. This is best performed spectroscopically using known extinction coefficients or against known standards, since it is not possible to distinguish D, A and S with simple protein assays. The surface concentration of S is unimportant, because it is being used simply as a spacer and has no spectral properties in terms of visible absorption or fluorescence. After correcting for the increase in volume attributable to the addition of the imidazole (typically a factor of 1.25×after adding a ¼ volume of a 5 M solution), surface concentrations of donor molecules on pure donor beads can be determined from the following:

$$[D] = \frac{[D]_{\text{Released in solution}}}{[B]\pi d^2} \quad (40)$$

where d is the bead diameter which is given by the manufacturer, or alternatively measured using a stage micrometer and known magnification factors. Bead concentration ([B]) in units of particles per ml, can be determined very accurately using a cell sorter. This has already been performed for three bead slurries, which were constructed under saturating fluorophore conditions. Fluorophore concentration measurements can be made for the pure acceptor and FRET beads using equations similar to equation (40). In the case of FRET beads, total donor and total acceptor concentrations can be determined after release.

Example 3

Data Acquisition for GFP-Labeled Beads

FIG. 3 shows a set of monochrome images obtained for a mixture of labeled Sephadex beads. Individual beads were coated with either (1) BFP-11 alone (donor beads), (2) RSGFP8 alone (acceptor beads) or (3) a 2:1 mixture of donor and acceptor (FRET beads). FIG. 3, lower right, shows the intensity of fluorescence emitted by all of the beads in the donor emission channel when excited by light corresponding to the donor's excitation spectrum. FIG. 3, lower left, shows the fluorescence emitted by the same beads in the acceptor channel when excited by light corresponding to the acceptor's absorption spectrum. FIG. 3, upper right, (the "FRET" channel) shows the fluorescence emitted in the acceptor channel when excited by light corresponding to the donor's excitation spectrum. The results from these monochrome images are displayed together in a pseudocolor image, with the fluorescence signal from the donor channel assigned the color blue, the signal from the acceptor channel assigned the color green, and the signal from the FRET channel assigned the color red (FIG. 3, upper left). In this image, the color intensities in each of the three channels are scaled to the pixel (from any of the three channels) with the highest grayvalue (DEFAULT setting). The FRET beads appear gold because these beads have fluorescence contributions in all three channels. The pure donor beads appear purple (blue-red) because these beads have fluorescence contributions from the donor (blue) and FRET (red) channels. The pure acceptor beads appear mostly green with a slight reddish color because these beads have fluorescence contributions from the acceptor (green) and FRET (red) channels. It is evident from these images that there is significant bleed-through of both donor and acceptor emission into the FRET channel.

Example 4

Image Acquisition of GFP-Labeled Beads

Three monochrome images were acquired using the set of three epifluorescence cubes (see, TABLE 1) to image a mixture of three different types of fluorescent beads (described in TABLE 2). The epifluorescence cubes and bead types are labeled Donor, Acceptor, and FRET to emphasize that the cubes and beads are spectrally matched. The donor bead carries a GFP derivative (BFP11) with an excitation maximum in the long wave UV and emission in the blue. The acceptor bead carries RSGFP4, which is excited maximally in the cyan and fluoresces in the green. These excitation and emission wavelengths are matched to the donor and acceptor cubes. The FRET bead carries both the blue and green GFP derivatives, and the corresponding FRET cube is optimized to excite the blue donor and image the green acceptor after energy transfer has occurred. Images acquired using the Donor, Acceptor, and FRET cubes are referred to as the D1, A1, and F1 images, respectively.

TABLE 2

Spectral characteristics of fluorescent beads used in this work. Wavelengths (nm) are given as $\lambda_{max}$.

| Bead/Derivative | Excitation | Emission |
| --- | --- | --- |
| Donor/BFP11 | 380 | 445 |
| Acceptor/RSGFP4 | 490 | 510 |
| FRET/BFP11 + RSGFP4 | 380 | 510 |

Spectral mixing among the donor, acceptor, and FRET beads can be observed in the spatially coregistered monochrome and RGB images of FIG. 3. In the D1 image, the donor beads are the brightest, but dimmer FRET beads are also observed. In the A1 image, the acceptor beads are the brightest, but dimmer FRET beads are also observed. In the F1 image, the FRET beads are the brightest, but dimmer donor beads are observed. This is consistent with the fluorescence spectra shown in FIG. 2 and the parameters given in TABLE 2. The pseudocolored, upper left image (RGB1) in FIG. 3 is the result of encoding the pixel values of each of these monochrome images into an intensity value for each of the red, green and blue components of the image. F1 is loaded into the red color channel, A1 is loaded into the green color channel and D1 is loaded into the blue color channel. Because of spectral overlap, the various bead types are not visually distinct or well defined in this RGB image.

Careful observation of the emission spectra of the donor and the acceptor shows that there is no wavelength at which the two fluorophores can be separated. For example, the use of a very narrow bandpass emission filter at 550 nm would not only fail to separate the two fluorophore's emissions, but it would also result in the loss of most of the microscope's light gathering ability. Using higher intensity illumination to compensate for this loss is likely to result in photobleaching. In contrast, the invention uses broad-band emission filters and a relatively low intensity excitation source.

Example 5

Color-Coded Images of Baculovirus-Infected Sf9 Cells

Figure 7:
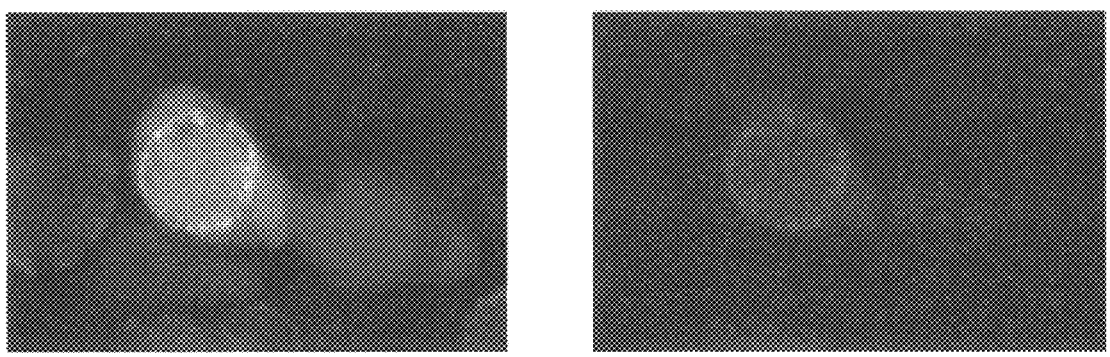
FIG. 7 is a set of spatially coregistered color-coded images which show Baculovirus-infected Sf9 cells expressing a blue-emitting derivative of GFP (i.e., BFP1 1), a green-emitting derivative with red-shifted excitation (i.e., RSGFP4), and a BFP1 I/RSGFP4 fusion protein that is efficient at FRET. The donor, acceptor, and FRET signals have been separated and pseudocolored blue, green, and red, respectively, by the qualitative MicroFRET imaging system based on picking candidate D, A, and F pixels.

Baculovirus-infected Sf9 cells expressing BFP11, RSGFP4, and a BFP11/RSGFP4 fusion protein were tested (as shown in FIG. 7). After proper calibration of the system using FRET Beads, the [D] values are equal to zero in the RSGFP4-infected cells, and [A] values are equal to zero in the BFP11-infected cells. FRET efficiencies in the BFP11/RSGFP4 fusion-protein-infected cells are equal to or less than the efficiency for the isolated fusion protein measured in solution, depending on the extent of proteolysis.

The extent of photobleaching and photoisomerization is less than 5%, as previously measured for the MicroFRET system using similar cubes, light sources, and CCD cameras.

Example 6

Measurement of Donor Photobleaching

Steady-state FRET imaging of cells by sensitized emission using conventional microscopy has previously suffered from an inability to correct for spectral overlap while maintaining spatial co-registration. Until now, the three epifluorescence cubes (donor, acceptor and FRET) that must be used to generate the correction values have been manufactured with optical surfaces that are not strictly parallel. This defect created geometric distortions in the image (i.e., displacement of pixels) after the images were combined. The MicroFRET instrument employs epifluorescence cubes which have been machined to precise tolerances, so that spatial co-registration is maintained for all of the images. This design also makes it feasible to detect relatively small amounts of FRET within a given pixel because the mathematical correction is much simpler (and therefore more accurate) than was previously possible.

The effectiveness of these corrections was demonstrated by obtaining images of Sepharose beads loaded with either BFP-11, RSGFP4 or a defined mixture of the two (which is known to generate FRET). By using these beads as calibration standards, spectral overlap was corrected for and features identified within the image displaying donor emission, acceptor emission and donor-sensitized acceptor emission (FRET). By subsequently applying the ortho normalization algorithm ("pixel purification"), the pure donor, pure acceptor and FRET beads were pseudocolored as blue, green and red, respectively.

Another concern in using the sensitized emission technique has been that the exciting light can photobleach the donor and thereby reduce the apparent intensity of the FRET signal. The sensitized emission technique does not reduce the FRET signal by more than 5% when using the method of the invention. Photobleaching is not a major problem because the high sensitivity of the K7 camera makes long exposures unnecessary. The grayscale intensities of the fluorescent signals in the experiments, for example, used approximately ⅓ of the total dynamic range of the camera (maximum=65535 bits). Nevertheless, under these exposure conditions, less than 5% of the donor signal was photobleached. The exposure time could easily be reduced by a factor of 10 and still allow the signal to be detected.

The maximum extent of photobleaching of the BFP-11 donor during a FRET measurement was determined by monitoring the intensity of fluorescence emission from a sample of donor beads which were repeatedly given 30 sec. exposures to the exciting light. The mean grayscale value was determined for ten randomly selected pixels after multiple exposures, and these values were compared to the values for the same beads after the initial 30 sec. exposure. The measured intensity of the fluorescence emission after repeated exposure to the exciting light was >95% of the initial level.

Example 7

Quantitative Fret Microscopy

The purpose of this EXAMPLE is to show that it is feasible to perform quantitative FRET microscopy by determining the donor concentration, acceptor concentration, energy transfer efficiency, and distance parameters between donor and acceptor molecules for every pixel in a microscopic field of view.

Quantitative Imaging was performed using an Olympus AX70 epifluorescence microscope equipped with three cubes matched to the excitation and emission spectra of the GFP derivatives (TABLE 3). These cubes were spatially coregistered to single-pixel accuracy. Images taken with each cube form the input of three channels, which were used for subsequent image processing. The $C_1$ channel was designed to selectively excite and image donor emission, the $C_2$ channel was designed to selectively excite and image acceptor emission and the $C_3$ channel was designed to visualize FRET, since excitation was at the donor excitation and imaged at the acceptor emission.

TABLE 3

Spectral characteristics of epifluorescence cubes used for BFP11/RSGFP4. Wavelengths (nm) are given as cut-on and cut-off (50% peak transmission) for excitation and emission filters and as the inflection point for dichroic filters.

| Cube | Excitation (nm) | Dichroic (nm) | Emission (nm) |
| --- | --- | --- | --- |
| Donor (BFP11) | 335–380 | 410 | 435–490 |
| Acceptor (RSGFP4) | 450–490 | 495 | 505–550 |
| FRET | 335–380 | 410 | 505–550 |

Example 8

Ortho normalization of Chromogenic Dyes

Figure 9:
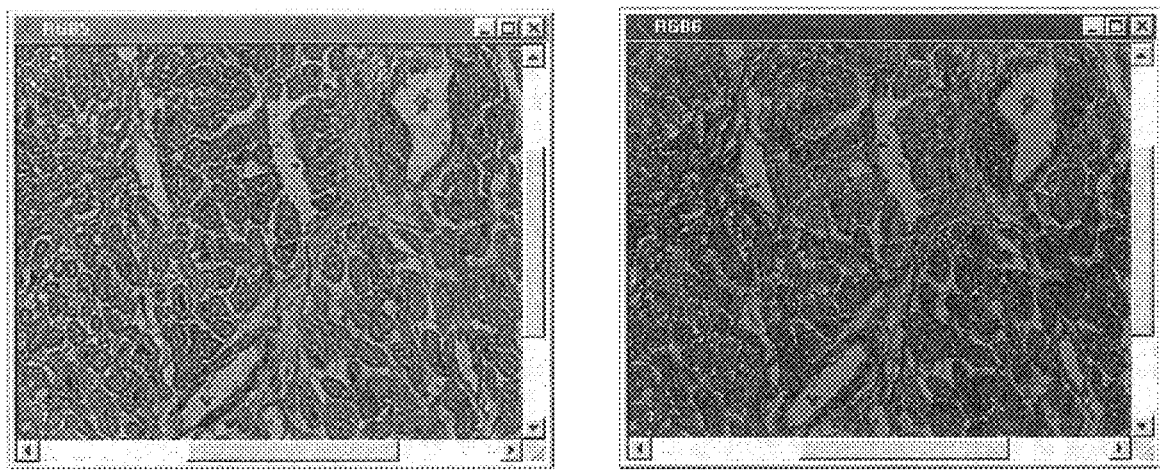
FIG. 9 shows hematoxylin and eosin (H&E) slides of stained thin sections of cardiac tissue including an infarct. The left panel shows the true-color image generated by combining three separate monochrome images at 450, 550, and 650 nm of the H&E stained tissue. The right panel shows this image after ortho normalization in accordance with the invention.

Color space transformation algorithms are useful for rapidly identifying and highlighting groups of pixels or features in images which have very subtle or overlapping color difference. For example, FIG. 9 shows hematoxylin and eosin (H&E) slides of stained thin sections of cardiac tissue including an infarct. The left panel shows the true-color image generated by combining three separate monochrome images at 450, 550, and 650 nm of the H&E stained tissue. The right panel shows this image after ortho normalization. In this particular case, candidate pixels for the ortho normalization were picked from nuclei, lightcolored eosin, and dark colored eosin-containing regions as R, G, and B, respectively. The resultant image shows two distinct types of eosinophilic tissue. Such differentiation in staining by eosin is difficult to see in non-enhanced images. Subtle color differences in eosin may correlate with various disease states such as the presence of collagen in tissues. The enhanced image has been further enhanced by contrast enhancement of each separate R, G, and B color channel.

Example 9

Corrections in Time-Course Imagery

Candidate pixels or features that are used to calculate the color space coordinates of the refined image can be selected from a sequence of spatially coregistered images which might, for example, involve a time sequence of events. In this embodiment, a series of images would be displayed within a window with 'stop', 'start', 'forward' and 'time-delay' parameters. While the sequence of images might have been obtained over a very fast time course (video rates; milliseconds per frame), the player would enable the end user to slow down the visualization process to the extent that candidate pixels would be picked as the basis for the color space transformation. Coefficients to these specific transformations would be applied to all frames in the image sequence; the heuristics of a user-desired morphology would utilize a graphical user interface to evaluate whether the candidate pixels were a good pick. This method may be very important in ratio-metric dynamic imaging of live cells, wherein movements of protein, ions, and other cellular components are reported through fluorescence and FRET. Other evaluation criteria for determining whether the candidate pixels were properly chosen include the segregation of colors onto known standard targets.

The mathematical coefficients determined during the conversion of an unprocessed to processed image utilizing an image containing known standards, can be saved and applied to an image containing no standards. This standardization template can be recalled and the coefficients used to correct subsequent images taken under similar conditions of illumination, optical filtration and recording.

A number of embodiments of the present invention have been described. Nevertheless, it will be understood that various modifications may be made without departing from the spirit and scope of the invention. For example, the invention described above is clearly not limited to FRET analyses of GFP derivatives on specific beads, but these experiments do demonstrate a reduction to practice of an imaging spectrophotometer and methods capable of detecting FRET. Accordingly, other embodiments are within the scope of the following claims.

What is claimed is:

1. A method for transforming an initial FRET image of a specimen to a processed FRET image, the initial image being represented by a set of pixels each having three color space coordinates, the method including the steps of:

(a) generating a corrected FRET image from the initial image by correcting for spectral overlap by applying a transformation of the following form to obtain a corrected FRET channel image $F^c$:

$$F^c = F^b - (F_d^{b/D_d^b}) \times D^b - (F_a^b/A_a^b) \times A^b$$

wherein $F^b$ are pixels of an initial FRET channel image, $D^b$ are pixels of an initial donor channel image, $A^b$ are pixels of an initial acceptor channel image, $F_d^b$ are donor pixels of the initial FRET channel image, $F_a^b$ are acceptor pixels of the initial FRET channel image, $D_d^b$ are donor pixels of the initial donor channel image, and $A_a^b$ are acceptor pixels of the initial acceptor channel image, all after background subtraction;

(b) selecting at least two image regions in the corrected FRET image, each image region including at least one pixel, wherein the image regions define at least two distinguishable spectral categories and do not substantially overlap spatially;

(c) performing a color space transformation on the corrected image, based on the color space coordinates of the pixels in each of the selected image regions, to generate a processed image; and (d) evaluating the processed image for a visible indication of an improved spatial distribution of color.

2. The method of claim 1, including the step of further correcting the corrected FRET image for cross-talk resulting from detection of donor fluorescence through an acceptor emission channel and detection of acceptor fluorescence through a donor emission channel.

3. The method of claim 1, including the step of further correcting the corrected FRET image for non-zero values of a signal Ad from a donor-only specimen using an acceptor filter set, and a signal Da from an acceptor-only specimen using a donor filter set.

4. The method of claim 1, including the step of further correcting the corrected FRET channel image $F^c$ by normalizing for the concentration of a donor present in the specimen.

5. The method of claim 1, including the step of further correcting the corrected FRET channel image $F^c$, so as to be approximately normalized for the concentration of a donor, by applying a correction of 1/Df, where Df is a signal generated through a donor filter set when both donors and acceptors are present in the specimen.

6. The method of claim 1, including the step of further correcting the corrected FRET channel image $F^c$ by normalizing for the concentration of an acceptor present in the specimen.

7. The method of claim 1, including the step of further correcting the corrected FRET channel image $F^c$, so as to be approximately normalized for the concentration of an acceptor, by applying a correction of 1/Af, where Af is a signal generated through an acceptor filter set when both donors and acceptors are present in the specimen.

8. The method of claim 1, including the step of further correcting the corrected FRET channel image $F^c$ by normalizing for the concentration of both a donor and an acceptor present in the specimen.

9. The method of claim 1, including the step of further correcting the corrected FRET channel image $F^c$, so as to be approximately normalized for the concentration of both a donor and an acceptor in the specimen, by applying a correction of 1/(Df×Af), where Df is a signal generated through a donor filter set when both donors and acceptors are present, and Af is a signal generated through an acceptor filter set when both donors and acceptors are present.

10. The method of claim 1, including the step of further correcting the corrected FRET image by correcting for cross-talk resulting from detection of donor fluorescence through an acceptor emission channel and detection of acceptor fluorescence through a donor emission channel, and by normalizing for the concentration of both a donor and an acceptor in the specimen.

11. The method of claim 1, wherein the extent of photobleachin of the initial FRET image is less than about 5%.

12. A computer program, residing on a computer-readable medium, for transforming an initial FRET image to a processed FRET image, the initial image being represented by a set of pixels each having three color space coordinates, the computer program comprising instructions for causing a computer to:

(a) generate a corrected FRET image from an initial image by correcting for spectral overlap by applying a transformation of the form to obtain a corrected FRET channel image $F^c$:

$$F^c = F^b - (F_d^b/D_d^b) \times D^b - (F_a^b/A_a^b) \times A^b$$

wherein $F^b$ are pixels of an initial FRET channel image $D^b$ are pixels of an initial donor channel image, $A^b$ are pixels of an initial acceptor channel image, $F_d^b$ are donor pixels of the initial FRET channel image, $F_a^b$ are acceptor pixels of the initial FRET channel image, $D_d^b$ are donor pixels of the initial donor channel image and $A_a^b$ are acceptor pixels of the initial acceptor channel image, all after background subtraction;

(b) select at least two image regions in the corrected FRET image, each image region including at least one pixel, wherein the image regions define at least two distinguishable spectral categories and do not substantially overlap spatially;

(c) perform a color space transformation on the corrected image, based on the color space coordinates of the pixels in each of the selected image regions, to generate a processed image; and (d) evaluate the processed image for a visible indication of an improved spatial distribution of color.

\* \* \* \* \*